(12) United States Patent
Lee et al.

(10) Patent No.: US 10,596,532 B2
(45) Date of Patent: Mar. 24, 2020

(54) ISOLATABLE AUTOMATIC DRUG COMPOUNDING SYSTEM

(71) Applicant: Zyno Medical, LLC, Natick, MA (US)

(72) Inventors: Chao Young Lee, Weston, MA (US); Mei Zhang, Sharon, MA (US)

(73) Assignee: Zyno Medical, LLC, Natick, MA (US)

( * ) Notice: Subject to any disclaimer, the term of this patent is extended or adjusted under 35 U.S.C. 154(b) by 151 days.

(21) Appl. No.: 15/811,881

(22) Filed: Nov. 14, 2017

(65) Prior Publication Data

US 2018/0133667 A1    May 17, 2018

Related U.S. Application Data

(60) Provisional application No. 62/422,700, filed on Nov. 16, 2016.

(51) Int. Cl.
*B01F 13/00* (2006.01)
*A61K 9/00* (2006.01)
(Continued)

(52) U.S. Cl.
CPC ............ *B01F 13/0022* (2013.01); *A61J 1/05* (2013.01); *A61J 1/14* (2013.01); *A61J 1/2048* (2015.05); *A61J 1/2051* (2015.05); *A61J 1/2058* (2015.05); *A61J 1/22* (2013.01); *A61K 9/0019* (2013.01); *A61K 9/08* (2013.01); *B01F 3/1271* (2013.01); *B01F 11/0005* (2013.01); *B01F 15/0022* (2013.01); *B01F 15/00194* (2013.01); *B01F 15/00311* (2013.01); *B01F 15/00974* (2013.01); *B01F 15/00993* (2013.01); *B08B 15/023* (2013.01); *B08B 15/026* (2013.01); *B01F 2215/0034* (2013.01)

(58) Field of Classification Search
CPC .... A61J 1/05; A61J 1/14; A61J 1/2048; A61J 1/2051; A61J 1/2058; A61J 1/22; A61K 9/0019; A61K 9/08; B01F 11/0005; B01F 13/0022; B01F 15/00194; B01F 15/0022; B01F 15/00311; B01F 15/00974; B01F 15/00993; B01F 2215/0034; B01F 3/1271; B08B 15/023; B08B 15/026
See application file for complete search history.

(56) References Cited

U.S. PATENT DOCUMENTS 3,000,292 A * 9/1961 Wojan ................... B08B 15/023
454/59
3,547,505 A * 12/1970 Ott ......................... A47B 37/00
312/1

(Continued)

FOREIGN PATENT DOCUMENTS

WO    WO-2015029018 A1 *   3/2015

*Primary Examiner* — Tony G Soohoo
(74) *Attorney, Agent, or Firm* — Boyle Fredrickson S.C.

(57) ABSTRACT

A low-cost drug compounding system that can practically fit inside of a fume hood or the like is provided. The system can use a single pump operable in forward and reverse directions (or multiple pumps) to compound complex mixtures particularly including those requiring the creation of solutions from dry or powdered ingredients. A wireless link allows operation of the system remotely. In one embodiment, the system uses a disposable mixing tube set that can be discarded after mixing while still attached to the base ingredient containers used for the compounding thereby minimize the chance of personnel exposure.

19 Claims, 2 Drawing Sheets

(51) Int. Cl.
*A61K 9/08* (2006.01)
*B01F 3/12* (2006.01)
*B01F 15/00* (2006.01)
*A61J 1/20* (2006.01)
*A61J 1/22* (2006.01)
*A61J 1/14* (2006.01)
*A61J 1/05* (2006.01)
*B01F 11/00* (2006.01)
*B08B 15/02* (2006.01)

(56) References Cited

U.S. PATENT DOCUMENTS

| | | | | |
|---|---|---|---|---|
| 4,587,793 A * | 5/1986 | Brennan | A61L 9/16 | 53/111 R |
| 5,159,799 A * | 11/1992 | Rising | B65B 3/003 | 53/433 |
| 5,466,220 A * | 11/1995 | Brenneman | A61J 1/2089 | 604/411 |
| 5,511,594 A * | 4/1996 | Brennan | A61J 3/00 | 141/100 |
| 5,628,665 A * | 5/1997 | Lang | H01J 9/395 | 445/73 |
| 5,711,705 A * | 1/1998 | Krainiak | A61L 2/208 | 454/57 |
| 5,730,765 A * | 3/1998 | Henry | B01L 1/02 | 96/420 |
| 5,792,435 A * | 8/1998 | Mueller | A61L 2/24 | 422/292 |
| 5,890,781 A * | 4/1999 | Ryder | B65B 69/00 | 312/1 |
| 5,897,526 A * | 4/1999 | Vaillancourt | A61M 5/162 | 604/411 |
| 5,997,928 A * | 12/1999 | Kaish | G07F 9/105 | 221/135 |
| 6,010,400 A * | 1/2000 | Krainiak | A61L 2/208 | 454/187 |
| 6,814,770 B2 * | 11/2004 | Lu | B08B 15/026 | 55/385.2 |
| RE38,747 E * | 6/2005 | Jagger | B65B 55/025 | 198/803.14 |
| 6,975,924 B2 * | 12/2005 | Kircher | B01F 13/1063 | 700/266 |
| 7,343,224 B2 * | 3/2008 | DiGianfilippo | A61K 9/0019 | 700/265 |
| 7,596,957 B2 * | 10/2009 | Fuhr | B25J 21/02 | 62/78 |
| 7,620,479 B2 * | 11/2009 | Kircher | B01F 13/1063 | 700/266 |
| 7,621,192 B2 * | 11/2009 | Conti | G01N 3/56 | 623/912 |
| 7,717,774 B2 * | 5/2010 | Rothbauer | A61L 2/00 | 454/187 |
| 8,940,065 B2 * | 1/2015 | Rindoks | B08B 15/023 | 454/56 |
| 9,005,166 B2 * | 4/2015 | Uber, III | A61M 5/007 | 604/131 |
| 2010/0305499 A1 * | 12/2010 | Matsiev | A61B 5/145 | 604/67 |

* cited by examiner

ISOLATABLE AUTOMATIC DRUG COMPOUNDING SYSTEM

CROSS-REFERENCE TO RELATED APPLICATION

This application claims the benefit of U.S. Provisional Application No. 62/422,700, filed Nov. 16, 2016.

BACKGROUND OF THE INVENTION

The present invention relates to systems for compounding drugs and in particular to systems that reduce operator exposure to drug ingredients during such compounding.

Medical drugs must often be prepared from base ingredients close to the time when they are administered in order to provide for maximum efficacy. For this reason, it is desirable to be able to prepare drug admixtures in a medical care environment such as a hospital or the like. For some drugs, however, the base ingredients can present risks to personnel who may be accidentally exposed to those ingredients particularly in concentrated form. This risk normally requires the use of specially trained personnel and in some cases a separate facility in which such admixtures can be created such as removes the mixing process from patients and hospital staff or the like.

SUMMARY OF THE INVENTION

The present invention provides a low-cost drug compounding system that can practically fit inside of a fume hood or the like. The system can use a single pump operable in forward and reverse directions (or multiple pumps) to compound complex mixtures particularly including those requiring the creation of solutions from dry or powdered ingredients. A wireless link allows operation of the system remotely. In one embodiment, the system uses a disposable mixing tube set that can be discarded after mixing while still attached to the base ingredient containers used for the compounding thereby minimize the chance of personnel exposure.

In one embodiment of the present invention, a drug compounding system includes an outer housing providing an internal cavity accessible through a door which may be opened and closed about the cavity; a peristaltic pump held within the internal cavity; a first shut off valve; a second shut off valve; a third shut off valve; and a controller executing a stored program stored in memory to: communicate with the program, the peristaltic pump, the first shut off valve, the second shut off valve, and the third shut off valve; and control operation of the peristaltic pump, the first shut off valve, the second shut off valve, and the third shut off valve according to the program; where the first, second, and third shut off valves and the peristaltic pump are configured to receive a mixing tube assembly having a central tube section providing a compliant wall surrounding a lumen for receipt of the central tube section by the peristaltic pump for pumping material through the central tube section by flexure of the wall of the central tube section and a branch connector communicating with a first end of the central tube section to provide conduits to a first and second flexible branch tubes joining the lumen of the central tube section to lumens of the first and second flexible branch tubes; and where the central tube fits within the first shut off valve configured to permit flow through the central tube in an open state and prevent flow through the central tube in a closed state, the first flexible branch tube fits within the second shut off valve configured to permit flow through the first flexible branch tube in an open state and prevent flow through the first flexible branch tube in a closed state, and the second flexible branch fits within the third shut off valve configured to permit flow through the second flexible branch tube in an open state and prevent flow through the first flexible branch tube in a closed state.

It is thus a feature of at least one embodiment of the invention to permit drug compounding within a sealed environment where the ingredients may be disposed of with the mixing tubing set without disconnection.

The door may provide an airtight seal of the internal cavity when in the closed state.

It is thus a feature of at least one embodiment of the invention to prevent exposure of drug ingredients, e.g., powders, to the environment and prevent contamination within the drug compounding system.

A port in the outer housing may provide for connection to a fume extraction system.

It is thus a feature of at least one embodiment of the invention to prevent fumes generated during drug compounding to enter the environment.

The outer housing may attach flexible gloves extending within the internal cavity and allowing an operator outside the outer housing to manipulate elements within the internal cavity.

It is thus a feature of at least one embodiment of the invention to allow the operator to open medicament containers and connect various connectors to those containers within a sterile environment.

The door may have a switch providing a door open condition to the controller to prevent operation of the peristaltic pump.

It is thus a feature of at least one embodiment of the invention to ensure an airtight environment within the glovebox.

A sensor may be held within the internal cavity and sensing fluid flow through the central tube section to analyze a chemical composition of a material flowing through the central tube section to establish a drug signature. The sensor may be a Raman spectrometer.

It is thus a feature of at least one embodiment of the invention to ensure proper compounding of the drug ingredients and to monitor fluid flow volumes.

The computer may execute the stored program stored in memory to: open the first and second shut off valves to permit fluid flow through the first flexible branch tube and central tube section and close the third shut off valve to prevent fluid flow through the second flexible branch tube; pump fluid in a forward direction from the first flexible branch tube to the central tube section; open the first and third shut off valves to permit fluid flow through the second flexible branch tube and central tube section and close the second shut off valve to prevent fluid flow through the first flexible branch tube; and pump fluid in a reverse direction from the central tube section to the second flexible branch tube.

It is thus a feature of at least one embodiment of the invention to allow a mixing fluid to be compounded with a dry drug ingredient and then refilled into a mixture receiving bag.

The system may have a sensor where the computer executes the stored program stored in memory to: detect a first amount of fluid pumped from the first flexible branch tube to the central tube section; and detect a second amount of fluid pumped from the central tube section to the second flexible branch tube.

It is thus a feature of at least one embodiment of the invention to know the amount of fluid volume within the IV tubes after trapped air is release to transfer the proper fluid volumes.

A second end of the central tube may communicate with a first connector adapted for attachment to a medicament vial, the first flexible branch tube may communicate with a second connector adapted for attachment to an IV bag, and the second flexible branch tube may communicate with a third connector adapted for attachment to a mixture receiving bag. The IV bag may contain a mixing fluid and the medicament vial contains a dissolvable drug ingredient.

It is thus a feature of at least one embodiment of the invention to allow for compounding of a dry drug ingredient with a mixing fluid.

A scale may be held within the internal cavity adapted to support the mixture receiving bag to provide a weight of the mixture receiving bag.

It is thus a feature of at least one embodiment of the invention to ensure the compounded medicament has the correct weight to ensure proper compounding.

A hanger may be held within the internal cavity for hanging the first IV bag positioned above the peristaltic pump.

It is thus a feature of at least one embodiment of the invention to allow intravenous drugs to be gravity fed into a medicament vial.

A mixer may be held within the internal cavity and configured to shake the medicament vial.

It is thus a feature of at least one embodiment of the invention to provide automatic mixing of dry ingredients with the mixing fluid.

In one embodiment of the present invention, a drug compounding tubing assembly includes a central tube section providing a compliant wall surrounding a lumen for receipt of the central tube section by a peristaltic pump for pumping material through the central tube section by flexure of the wall of the central tube section; a branch connector communicating with a first end of the central tube section to provide conduits to a first and second flexible branch tubes joining the lumen of the central tube section to lumens of the first and second flexible branch tubes; IV bag spikes attached to ends of the first and second flexible branch tubes adapted for attachment to a first and second IV bags to communicate between volumes of the first and second IV bags and lumens of the first and second flexible branch tubes; and a medicament cap connector communicating with a second end of the central tube section and adapted to be releasably attached to a medicament container to communicate between a volume of the medicament container and the lumen of the central tube section.

It is thus a feature of at least one embodiment of the invention to provide a tubing system to be used in the drug compounding system that is cheap and disposable.

The medicament cap connector may have a filtered vent permitting air to exit the medicament vial when the medicament cap connector is attached to the medicament vial.

It is thus a feature of at least one embodiment of the invention to allow gas trapped within the tubing to escape during the mixing process.

The medicament cap connector may have a siphon tube extending into the medicament vial when the first connector is attached to the medicament vial.

It is thus a feature of at least one embodiment of the invention to allow the admixture to be pumped from the medicament vial to a mixture receiving bag.

The medicament cap connector is a spike adapted for attachment to the medicament container.

It is thus a feature of at least one embodiment of the invention to allow for removable interconnection of the tubing with the medicament vial.

The first and second flexible branch tubes may be polyvinyl chloride (PVC) tubing. The central tube section may be silicone rubber tubing.

It is thus a feature of at least one embodiment of the invention to provide biocompatible tubing where the central tube section is flexible for flexing use with peristaltic pumps.

The branch connector may be a T-connector providing fluid communication between the first end of the central tube section and the first and second flexible branch tubes.

It is thus a feature of at least one embodiment of the invention to allow for interconnection of at least three separate medical tubing.

These particular objects and advantages may apply to only some embodiments falling within the claims and thus do not define the scope of the invention.

DETAILED DESCRIPTION OF THE PREFERRED EMBODIMENT

Figure 1:
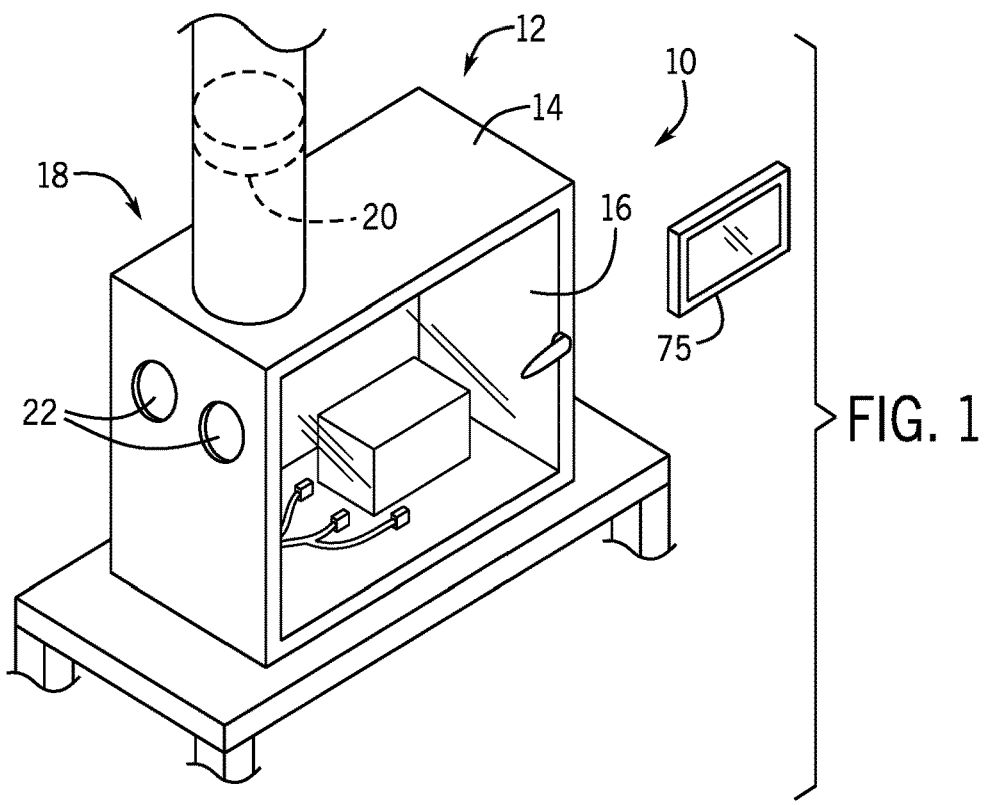
FIG. 1 is a perspective view of a glove box adapted for use with the present invention providing a closed, negative pressure environment for drug compounding.

Referring now to FIG. 1, the compounding system 10 of the present invention may work within a glovebox 12, the latter providing a generally box-shaped enclosure 14 sealable in an airtight manner by an openable front door 16. Alternatively, a double door can be implemented for added safety. The enclosure 14 may include an exhaust port 18 communicating with a fan system 20 drawing air out of the enclosure 14 and filtering this exhaust air for discharge safely out of the building and thereby creating a negative pressure in the enclosure 14 reducing the chance of escape of materials therefrom.

Apertures 22 in a side wall of the enclosure 14 may attach to flexible airtight gloves extending within the enclosure 14 allowing an operator outside of the enclosure 14 to manipulate elements inside the enclosure 14 as will be discussed.

Figure 2:
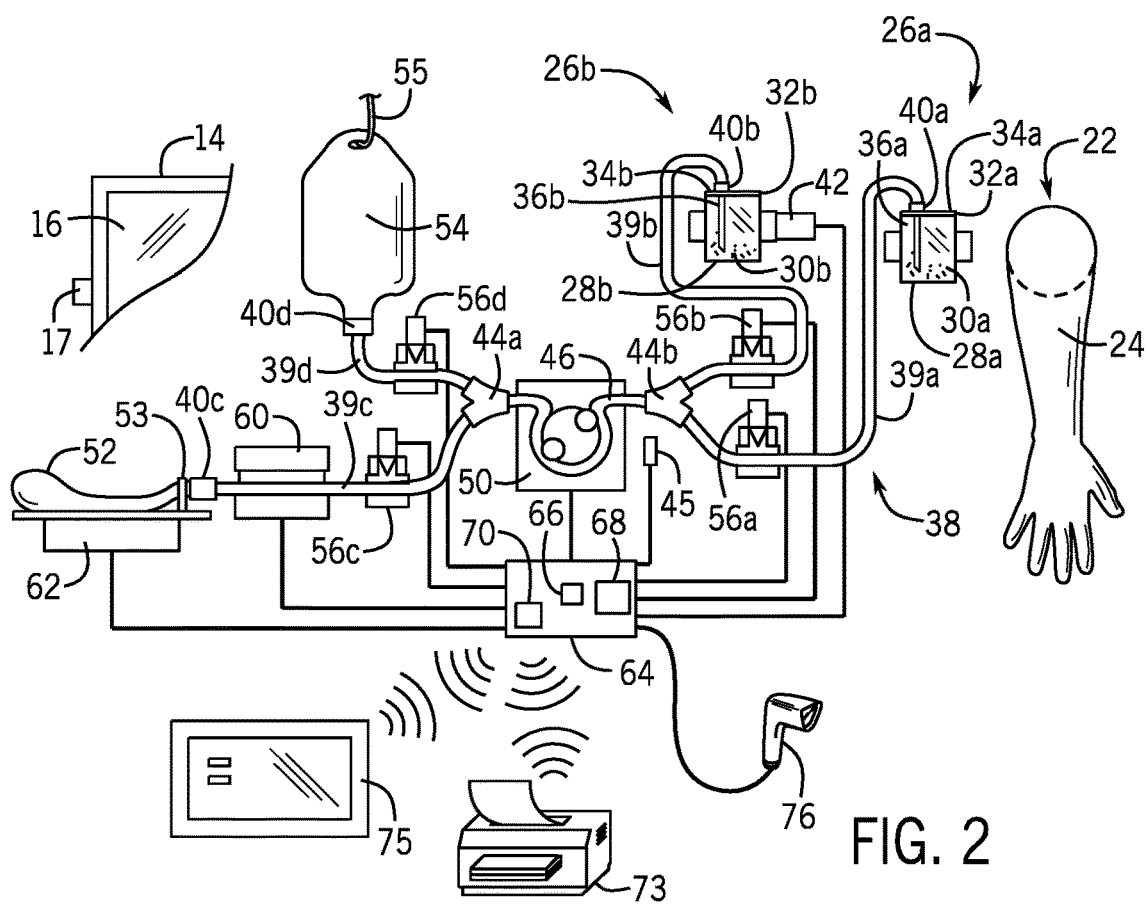
FIG. 2 is a simplified diagram of the compounding system that may fit within the glove box of FIG. 1 including a controller controlling a pump and multiple valves.
Figure 3:
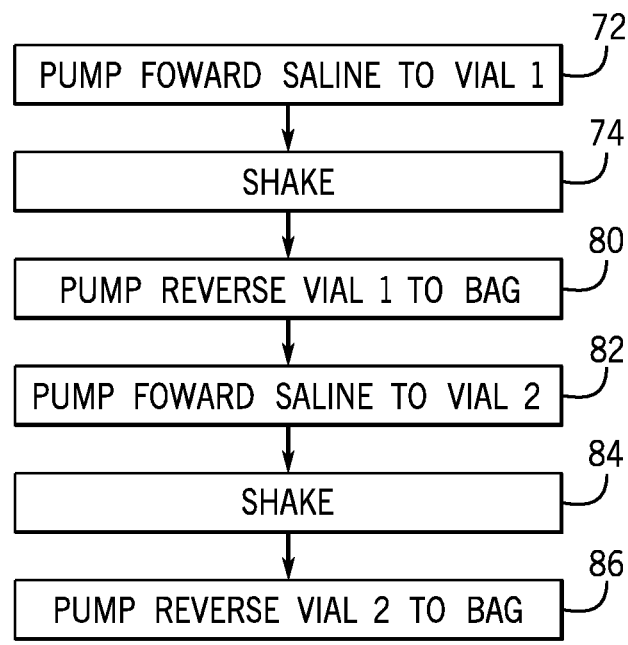
FIG. 3 is a flowchart showing operation of the pump and valves of the compounding system of FIG. 2 for an example compounding process.

Referring now to FIG. 2, gloves 24 attached to the apertures 22 may be proximate to a drug ingredient mount 26a holding a first vial 28a containing a powdered drug ingredient 30a. The vial 28a is generally sealed by a cap 32a having a filtered vent 34a permitting the passage of air out of the vial 28a without the escape of the drug ingredient 30a and having a siphon tube 36a attachable to a mixing tube set 38 by means of a connector 40a. Alternatively, the filtered vent or siphon tube can be one element integrated on the connector 40a, instead of on the cap of the vial. In this way standard vials may be used. The filtered vent 34a may have a check valve to block fluid flow but permit gas flow out of the vial 28a.

During operation, liquid will pass from a branch tube 39*a* and its associated connector 40*a* into the vial 28*a* to mix with the drug ingredients 30*a* as air escapes through the filtered vent 34*a*. An operator at particular times may use the glove 24 to remove the vial 28*a* from the mount 26*a* to shake the vial 28*a*, ensuring complete dissolving of the drug ingredient 30*a*. These manual processes can be completed by a robot arm inside the box as well or alternatively.

Alternatively, or in addition, a second mount 26*b* may be provided holding a second vial 28*b* with a second drug ingredient 30*b* and having a second vent 34*b* and siphon 36*b*, the latter attached to a second connector 40*b* leading to a second branch tube 39*b*. In this case the second mount 26*b* may include an electromagnetic actuator 42 (such as a motor and eccentric weight) that can be used to shake the vial 28*b* without operator intervention.

Figure 4:
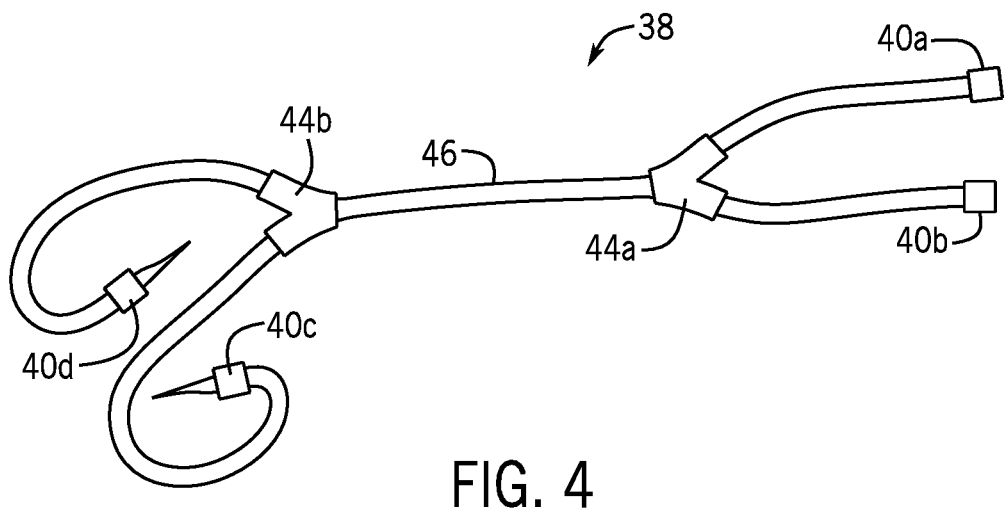
FIG. 4 is a figure of a disposable mixing tube set suitable for use with the present invention.

Referring also to FIG. 4, connectors 40*a* and 40*b*, attached to separate flexible branch tubes 39*a* and 39*b* respectively of the mixing tube set 38, are next received by a T connector 44*a* where they join into a single pliable pump tube 46 (for example, of silicone rubber or polyvinylchloride (PVC)) that may be installed in a peristaltic pump 50 or the like capable of pumping material through the pliable pump tube 46 without contact with that material in the pliable pump tube 46. The branch tubes 39 may be of flexible materials such as silicone or polyvinylchloride (PVC).

The opposite end of the pliable pump tube 46 may connect to a second T connector 44*b* separating into two branch tubes 39*c* and 39*d*, respectively, one providing a tube leading to a connector 40*c* attached, for example, to a mixture-receiving bag 52 and the other communicating with a connector 40*d* attached to a saline bag 54 containing a standard saline solution. The saline bag 54 may be hung by an IV bag hook 55 to suspend the saline bag 54 above the peristaltic pump 50.

The connectors 40*a*, 40*b* may be vented or unvented spikes that may be used to connect to a vial as is generally understood in the art. The connector 40*a*, 40*b* may also be a cap 32*a*, 32*b* secured to the vial 28*a*, 28*b* and providing a filtered vent 34*a*, 34*b* and/or siphon tube 36*a*, 36*b* as part of the mixing tube set 38.

The connectors 40*c*, 40*d* may be vented or unvented bag spikes that may be used to connect to an IV bag as is generally understood in the art.

Each of the components of the connectors 40*a*, 40*b*, 40*c*, 40*d*, the T connector 44*a* and 44*b*, the pliable pump tube 46, and the branch tubes 39 interconnecting these components, may be an integrated unit, factory sealed together at the time of manufacture, and disposed of without disassembly.

Each of branch tubes 39*a*-39*d* may pass through corresponding constriction valves 56*a*-56*d* positioned along their length between associated connectors 40 and T connectors 44. These constriction valves 56 operate by squeezing the branch tubes 39 to closure when activated thus providing a valve action that does not contact the material within the branch tubes 39.

The branch tube 39*c* may also pass through a spectrometer 60, for example, a Raman spectrometer that allows evaluation of the contents of the material flowing into bag 52. Such a spectrometer 60 is described, for example, in U.S. provisional application 62/280,999 entitled Apparatus and Method for Delivery-Contemporaneous Medicine Verification filed Jan. 20, 2016, and hereby incorporated by reference. Other elements including those providing for barcoding, visual inspection, drug signature generation, and reporting for a drug may also be employed with the present invention. In this regard, the bag 52 may be placed on a scale 62 providing a weight of the bag as it fills and upon completion of filling.

Each of the pump 50 valves, 56 electromagnetic actuator 42, scale 62, and spectrometer 60 may communicate with a computerized controller 64, for example, providing one or more processors 66 communicating with a stored program 68 that can execute a sequence as will be described. The controller 64 may also include a wireless transceiver 70, for example, providing Bluetooth or Wi-Fi interconnection with a separate control computer 75 such as a tablet computer, desktop computer, or the like. This wireless connection allows operator control of the compounding system 10 without opening of the glovebox 12. The control of the valves can also be automatically realized by a computer program for a specific mixing process that does not need user intervention.

In this respect, the controller 64 may communicate with a control computer 75 to receive operator instructions and receive compounding information to perform the drug mixing process. For example, the control computer 75 may receive information related to the fluid flow through the mixing tube set 38 and the associated volume of fluid being pumped, as opposed to air, between the vials 28*a* and 28*b* and saline bag 54 and receiver bag 52. Similarly, the controller 64 may report the results of those processes to the control computer 75 for accounting purposes, for example, to track drug usage downstream with respect to delivery to a patient.

The controller 64 may also receive a door open signal indicating when the front door 16 is open or ajar and to send a signal to the controller to alert the operator that the front door 16 is not airtight sealed in a closed state and to prevent further operator control of the compounding system 10 until the door 16 is properly closed.

Referring now to FIGS. 2 and 4, in an example compounding sequence, a mixing tube set 38 may be attached to vials 28*a* and 28*b* and to saline bag 54 and receiver bag 52 with low risk of exposure to a user through the use of standard medical coupling technologies. This assembly may then be installed within the enclosure 14 feeding the appropriate branch tubes 39 through their corresponding valves 56 and pliable pump tube 46 being threaded into the peristaltic pump 50. A bar code reader 76 or the like may be used to read labels on the vials 28*a* 28*b* and saline bag 54 and receiver bag 52, for example, prompted by illuminated lamps next to each of these items or occurring automatically by means of self-contained RFID tags or bar code readers or the like, and may be incorporated into the stations where these elements are naturally supported within the enclosure 14. Prior to this time, a bar code may be printed by the computer 75 using printer 73 for placement on the receiving bag 52 and the computer 75 may receive, for example, from a central server, compounding instructions for a medicine for a particular patient that will be used to control the process as described and which will be used as a checklist against which to compare the contents of the vials 28 and is a manifest to make the barcode that is printed on the receiving bag 52.

Once the proper materials have been loaded, an operator command may be provided and valves 56*d* and 56*a* may open while valves 56*c* and 56*b* are closed, and the pump 50 may be operated in a forward direction to deliver saline from bag 54 to vial 28*a* as indicated by process block 72.

Per process block 74, vial 28*a* may then be shaken, for example, manually or by use of an actuator 42 or the like.

Per process block 80, valve 56d may then be closed and valve 56c opened, and pump 50 may then be operated in reverse direction to draw liquid from vial 28a to the receiver bag 52 while its compounded material is monitored by the spectrometer 60 and the scale 62.

Valves 56c and 56a may then be closed and valves 56d and 56b opened so that material can be pumped by the pump 50 from the saline bag 54 to the vial 28b per process block 82. At process block 84, vial 28b may be shaken and then at process block 86, valve 56d closed and valve 56c opened to transfer material into the receiving bag 52.

Upon completion of this mixing process, a portion of the material in the receiving bag 52 may be drawn backward through the spectrometer 60 into one of the vials 28 to provide more complete mixing and to provide a signature of the final drug in receiving bag 52 (e.g., both weight and constitution). This signature may be used to track drug usage and/or disposal through the lifecycle of the drug in bag 52, for example, as described in the above referenced U.S. patent application 62/280,999. Drug identification can also be completed by obtaining spectrum signature from the fluid inside the bag by placing the spectrometer near the bag.

In another example of a compounding sequence transmitted to the control computer 75 to display operator instructions to perform the drug mixing process, the operator instructions may prompt the user to install the mixing tube set 38 within the enclosure 14 feeding the appropriate branch tubes 39 through their corresponding valves 56 and the pliable pump tube 46 being threaded into the peristaltic pump 50.

An operator command may be provided and all valves 56a, 56b, 56c, and 56d may then be closed. Once all valves are shut, the user may be prompted to hang the saline bag 54 on the IV bag hook 55 and place the receiver bag 52 on the scale 62 and attach the connector 40c of branch tube 39c and connector 40d of the branch tube 39d to the receiver bag 52 and saline bag 54, respectively. The vials 28a, 28b may be installed on drug ingredient mounts 26a, 26b and the door 16 of the enclosure 14 may be closed over the door opening to provide an airtight sealed.

The user may use flexible airtight gloves 24 extending within the enclosure 14 to connect connectors 40a and 40b of the mixing tube set 38 to the vials 28a, 28b.

Once the proper materials have been loaded, an operator command may be provided and valves 56d and 56a may open while valves 56c and 56b are closed, and to operate the pump 50 in a forward direction to deliver saline from bag 54 to the vial 28a. A liquid sensor 45 or the like arranged immediately before or immediately after the pump 50 at a location between the first T-connector 44a and second T-connector 44b may detect the flow of fluid through the pliable pump tube 46. In this respect, the liquid sensor 45 may sense the amount of saline delivered to the vial 28a as opposed to air trapped within the mixing tube set 38. The liquid sensor 45 may be a sensor as described in U.S. Pat. No. 9,242,037 entitled "Flow sensor for medical pump" and filed Dec. 12, 2013 and U.S. Pat. No. 9,327,072 entitled "Multifunction capacitive sensor for medical pump" filed Dec. 12, 2013, both of which are hereby incorporated by reference. The filtered vent 34a of the vial 28a may allow air trapped within the mixing tube set 38 to escape from the vial 28a while saline is pumped into the vial 28a. The liquid sensor 45 allows the control computer 75 to determine the amount of liquid is within the mixing tube set 38 when valves 56d and 56a are open and valves 56c and 56b are closed to monitor the volume of saline delivered to the vial 28a.

Once the desired volume of saline is transferred to the vial 28a, the vial 28a may then be shaken, for example, manually or by use of an actuator 42 or the like.

The valve 56d may then be closed and valve 56c opened, and pump 50 may then be operated in reverse direction to draw liquid from vial 28a to the receiver bag 52. The liquid sensor 45 may detect the flow of fluid through the pliable pump tube 46. In this respect, the liquid sensor 45 may sense the amount of liquid delivered to the receiver bag 52 as opposed to air trapped within the mixing tube set 38. The receiver bag 52 may be vented to allow air trapped within the mixing tube set 38 to escape from the receiver bag 52 while the liquid is pumped into the receiver bag 52. The liquid sensor 45 allows the control computer 75 to determine the amount of liquid is within the mixing tube set 38 when valves 56c and 56a are open and valves 56d and 56b are closed to monitor the volume of liquid delivered to the receiver bag 52.

Similar to the process described with respect to vial 28a, the process may be repeated whereby valves 56c and 56a may then be closed and valves 56d and 56b opened so that material can be pumped by the pump 50 from the saline bag 54 to the vial 28b. Vial 28b may be shaken and valve 56d closed and valve 56c opened to transfer material into the receiving bag 52.

Upon completion of this mixing process, a clamp 53 or the like proximate the neck of the receiving bag 52 may be closed for example, manually or by use of an automatic clamp controlled by the controller 64.

The operator instructions may prompt the user to open the door 16 and disconnect the connector 40c from the receiving bag. The receiving bag 52 may be removed from the enclosure 14 for administration to the patient.

The user may remove the mixing tube set 38 from the valves 56 and the peristaltic pump 50, remove the saline bag 54 from the IV bag hook 55, and remove vials 28a, 28b from the drug ingredient mounts 26a, 26b. The entire mixing tube set 38, saline bag 54 and vials 28a, 28b may then be disposed of without disassembly.

It will be appreciated generally that the present invention provides a compact unit for compounding drugs that minimizes operator exposure allowing disposal of all drug-contacting materials.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors or other types of computers, gate arrays or the like that can execute programs and communicate with each other. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A drug compounding system comprising:
    an outer housing providing an internal cavity accessible through a door which may be opened and closed about the cavity;
    a peristaltic pump held within the internal cavity;
    a first shut off valve;
    a second shut off valve;
    a third shut off valve; and
    a controller executing a stored program stored in memory to:
        communicate with the program, the peristaltic pump, the first shut off valve, the second shut off valve, and the third shut off valve; and
        control operation of the peristaltic pump, the first shut off valve, the second shut off valve, and the third shut off valve according to the program;
    wherein the first, second, and third shut off valves and the peristaltic pump are configured to receive a mixing tube assembly having a central tube section providing a compliant wall surrounding a lumen for receipt of the central tube section by the peristaltic pump for pumping material through the central tube section by flexure of the wall of the central tube section and a branch connector communicating with a first end of the central tube section to provide conduits to a first and second flexible branch tubes joining the lumen of the central tube section to lumens of the first and second flexible branch tubes; and
    wherein the central tube fits within the first shut off valve configured to permit flow through the central tube in an open state and prevent flow through the central tube in a closed state, the first flexible branch tube fits within the second shut off valve configured to permit flow through the first flexible branch tube in an open state and prevent flow through the first flexible branch tube in a closed state, and the second flexible branch fits within the third shut off valve configured to permit flow through the second flexible branch tube in an open state and prevent flow through the first flexible branch tube in a closed state; and
    further comprising a sensor held within the internal cavity and sensing fluid flow through the central tube section to analyze a chemical composition of a material flowing through the central tube section to establish a drug signature.

2. The drug compounding system of claim 1 wherein the door provides an airtight seal of the internal cavity when in the closed state.

3. The drug compounding system of claim 1 further comprising a port in the outer housing for connection to a fume extraction system.

4. The drug compounding system of claim 1 wherein the outer housing attaches flexible gloves extending within the internal cavity and allowing an operator outside the outer housing to manipulate elements within the internal cavity.

5. The drug compounding system of claim 1 wherein the door has a switch providing a door open condition to the controller to prevent operation of the peristaltic pump.

6. The drug compounding system of claim 1 wherein the sensor is a Raman spectrometer.

7. The drug compounding system of claim 1 wherein the controller executes the stored program stored in memory to:
    open the first and second shut off valves to permit fluid flow through the first flexible branch tube and central tube section and close the third shut off valve to prevent fluid flow through the second flexible branch tube;
    pump fluid in a forward direction from the first flexible branch tube to the central tube section;
    open the first and third shut off valves to permit fluid flow through the second flexible branch tube and central tube section and close the second shut off valve to prevent fluid flow through the first flexible branch tube; and
    pump fluid in a reverse direction from the central tube section to the second flexible branch tube.

8. The drug compounding system of claim 7 further comprising a sensor wherein the computer executes the stored program stored in memory to:
    detect a first amount of fluid pumped from the first flexible branch tube to the central tube section; and
    detect a second amount of fluid pumped from the central tube section to the second flexible branch tube.

9. The drug compounding system of claim 1 wherein a second end of the central tube communicating with a first connector adapted for attachment to a medicament vial, the first flexible branch tubes communicating with a second connector adapted for attachment to an IV bag, and the second flexible branch tube communicating with a third connector adapted for attachment to a mixture receiving bag.

10. The drug compounding system of claim 9 further comprising a scale held within the internal cavity adapted to support the mixture receiving bag to provide a weight of the mixture receiving bag.

11. The drug compounding system of claim 9 further comprising a hanger held within the internal cavity for hanging the first IV bag positioned above the peristaltic pump.

12. The drug compounding system of claim 9 further comprising a mixer held within the internal cavity and configured to shake the medicament vial.

13. The drug compounding system of claim 9 wherein the IV bag contains a mixing fluid and the medicament vial contains a dissolvable drug ingredient.

14. The drug compounding system of claim 1 further comprising a mixing tube assembly having
    a central tube section providing a compliant wall surrounding a lumen for receipt of the central tube section by a peristaltic pump for pumping material through the central tube section by flexure of the wall of the central tube section;

a branch connector communicating with a first end of the central tube section to provide conduits to a first and second flexible branch tubes joining the lumen of the central tube section to lumens of the first and second flexible branch tubes;

IV bag spikes attached to ends of the first and second flexible branch tubes adapted for attachment to a first and second IV bags to communicate between volumes of the first and second IV bags and lumens of the first and second flexible branch tubes; and a medicament cap connector communicating with a second end of the central tube section and adapted to be releasably attached to a medicament container to communicate between a volume of the medicament container and the lumen of the central tube section.

15. The drug compounding system of claim 14 wherein the medicament cap connector has a filtered vent permitting air to exit the medicament vial when the medicament cap connector is attached to the medicament vial.

16. The drug compounding system of claim 14 wherein the medicament cap connector has a siphon tube extending into the medicament vial when the first connector is attached to the medicament vial.

17. The drug compounding system of claim 14 wherein the medicament cap connector is a spike adapted for attachment to the medicament container.

18. The drug compounding system of claim 14 wherein the central tube section is a silicone rubber tubing.

19. The drug compounding system of claim 14 wherein the branch connector is a T-connector providing fluid communication between the first end of the central tube section and the first and second flexible branch tubes.

* * * * *